(12) United States Patent
Gwon et al.

(10) Patent No.: US 6,410,544 B1
(45) Date of Patent: *Jun. 25, 2002

(54) CHOLINERGIC AGENTS IN THE TREATMENT OF PRESBYOPIA

(75) Inventors: Arlene Gwon, Newport Beach; Elizabeth WoldeMussie, Laguna Niguel, both of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/842,299

(22) Filed: Apr. 25, 2001

Related U.S. Application Data

(63) Continuation-in-part of application No. 09/126,064, filed on Jul. 30, 1998, now Pat. No. 6,291,466.

(51) Int. Cl.[7] ............................................ A61K 31/505
(52) U.S. Cl. ...................................... 514/256; 514/912
(58) Field of Search ................................. 514/256, 912

(56) References Cited

U.S. PATENT DOCUMENTS 5,122,522 A * 6/1992 Laties et al. ................. 514/220

* cited by examiner

*Primary Examiner*—Zohreh Fay
(74) *Attorney, Agent, or Firm*—Walter A. Hackler

(57) ABSTRACT

A method for increasing or decreasing parasympathetic/cholinergic/ciliary tonic contraction in order to restore the resting portion of the eye and allow normal positive and negative accommodation includes administering to a myopic or hyperopic presbyope.

13 Claims, No Drawings

CHOLINERGIC AGENTS IN THE TREATMENT OF PRESBYOPIA

This application is a continuation in part of Ser. No. 09/126,064 filed on Jul. 30, 1998, now U.S. Pat. No. 6,291,466.

The present application is a continuation-in-part of U.S. Ser. No. 09/126,064 filed Jul. 30, 1998, now abandoned.

Presbyopia, occurring after middle age, is the inability of an eye to focus correctly. This age-related ocular pathology manifests itself in a loss of accommodative ability. Accommodative ability is the capacity of the eye, through the lens, to focus on near or far objects by changing the shape of the lens to become more spherical, or convex. A person may be a myopic presbyope or a hyperopic presbyope.

The ciliary muscle controls the shape of the lens through suspended suspensory ligaments called zonules. Like most smooth muscles, the ciliary muscle has a dual innervation, receiving both sympathetic and parasympathetic fibers.

In the ciliary muscle, the contraction necessary for accommodation is under parasympathetic or cholinergic control. While this parasympathetic control is predominant, sympathetic, or adrenergic, innervation opposes the cholinergic control and plays a lesser role in enabling relaxation of the ciliary muscle.

Most current theories of accommodation assume that the condition of physiological rest of accommodation occurs when the emmetropic eye focuses on a distant target, demanding good resolution. The fact that the optical value for the location of this distant target can be stated as zero diopters from the eye has tended to perpetuate the concept that active accommodation is unidirectional toward a near object.

However, if one considers that if the normal stimulus to accommodation is visual in nature, then the resting state of the eye must be determined by removing all visual stimuli, as for example, in complete darkness or in a luminous but completely empty visual field. This state of rest of the eye has been called "tonic accommodation", "space myopia" and "sky myopia", and averages about 1 D in extremely low illumination or total darkness but may be as high as 2 D myopia.

This implies that the resting state of accommodation is present when the eye is focused for objects about one meter away. Accordingly, distant objects would be focused on the retina by an active negative accommodation and near objects would be focused by an active positive accommodation.

Accordingly, in the natural resting state of the eye, the parasympathetic/cholinergic system maintains ciliary muscle tone, i.e., the ciliary muscle is contracted and zonular tension is relaxed such that the lens is more spherical and in a forward position increasing the refractive power of the eye. Thus, the eye is naturally in a "tonic accommodative" state and with appropriate stimulus is capable of further active positive accommodation as well as active negative accommodation.

SUMMARY OF THE INVENTION

A method in accordance with the present invention provides for increasing or decreasing parasympathetic/cholinergic/ciliary tonic contraction in order to restore the resting position of the eye and allow normal positive and negative accommodation for both myopic and hyperopic presbyopes. This action of the ciliary muscle under parasympathetic innervation provides for zonules relaxation which allows the lens to assume a more spherical shape.

A specific method in accordance with the present invention comprises administering to a presbyopic subject an effective amount of a muscarinic agonist or antagonist.

The agonist/antagonist is administered in a pharmaceutically acceptable ophthalmic formulation, preferably the agonist is administered topically by application of the formulation to the eye in a non-irritating sterile solution or suspension. In that regard, the formulation is preferably at a pH compatible with the eye. More particularly, in accordance with the present invention, a muscarinic agent may be selected to act on various M receptors of the ciliary muscle.

DETAILED DESCRIPTION

While not limiting the treatment of this invention to the validity of one proposed mechanism of action, it is believed that the action of circular fibers of the ciliary muscle causes relaxation of the zonules and allows greater curvature or sphericity of the lens. The radial/longitudinal fibers of the ciliary muscle relax, or stretch, which allows the lens to move forward. However, as the lens continues to grow throughout life, its increased size and concomitant loss of elasticity exceeds the capability of the ciliary muscle to effect a proper accommodation change. In addition, the resting state of the eye is also expected to change. This applies to both myopic and hyperopic presbyopes.

In addition, aging studies on the brain have demonstrated a loss of function of the cholinergic system that is due to a decline in the neurotransmitter substance acetylcholine. This is probably due to a decreased production by the enzyme cholineacetyl transferate (CHAT) acetylcholine synthetase as there is no decline in cholinergic receptor cells with age. That is, the ciliary muscle has the same number of receptors and the contractile ability of the muscle is the same in young and old individuals.

In accordance with the present invention, muscarinic receptor subtypes enable selective contraction or relaxation of the circular or longitudinal fibers of the ciliary muscle by action on the $M_1$–$M_5$ receptors.

A summary of receptor subtypes is given in Table 1.

TABLE 1

| Receptor subtype | Tissue or cellular function | Signaling mechanisms |
| --- | --- | --- |
| $M_1$ | Contraction or secretion | PI, Ca |
| $M_2$ | Relaxation | cAMP |
| $M_3$ | Contraction or secretion | PI, Ca |
| $M_4$ | Relaxation | cAMP |
| $M_5$ | Contraction or secretion | PI, Ca |
| Where | | |
| PI | Phosphoinositide hydrolysis (stimulatory response) | |
| Ca | Increase in intracellular free calcium (stimulatory response) | |
| cAMP | Increase in cyclic adenosine monophosphate (AMP) formation (inhibitory response) | |

The $M_3$ receptor subtype is the most common and is seen predominantly in the circular fibers and the $M_5$ receptor is predominant in the longitudinal fibers. Accordingly, it is possible that the inhibition of the $M_5$ receptor and/or stimulation of the sympathetic nervous system may allow the relaxation/stretching of the longitudinal fibers.

The compounds useful in practicing the present invention are any muscarinic agonists or antagonists. As used herein, the term "muscarinic agonists" means any compound that produces a net sympatholytic response at autonomic neuro-effective junctions. Parasympatholytic agents which block the parasympathetic system are muscarinic antagonists and parasympathomimetic agents which stimulate the parasympathetic system are muscarinic agonists. Neuro-effective junctions are considered cholinergic if energized by muscarinic agonists such as acetylcholine.

Without limiting the present invention to specific groups and compounds listed, the following is a list of representative muscarinic agonists and antagonists useful in the present invention:

Muscarinic Agonists

In general, muscarinic agonists are M nonselective and are parasympathomimetic and stimulate the parasympathetic system. Such muscarinic agonists include, but not limited to:
Philocarpine
Isopilocarpine lactam
Carbachol
Bethanechol
Methacholine
Muscarine Muscarinic Antagonists Muscarinic antagonists are parasympatholytic and block the parasympathetic system.

These antagonists have higher affinity for the designated receptors, but they also bind to the other receptor subtypes with a lower affinity. Such muscarinic antagonists include, but not limited to, in relation to M receptors:

$M_1$ Pirenzepine, Telenzepine, $(M_1/M_4)$trihexyphenidyl $M_2$  (+)(11-({2-[(diethylaminomethyl]-1-piperdidinyl}acetyl)-5,11-di-hydro-6H-pyrido(2,3-b)(1, 4)benzodiazepine-6-one; (+)5,11 dihdro-11-{[2-[(dipropylamino)methyl]-1piperidinyl)amino]carbonyl}-6H-pyrido(2,3-b)(1,4)benzodiazepine-6-one; himbacine, triptiramine $M_3$ diphenylacetoxy-N-methlypiperidine methiodide, (+)p-fluro-hexahydro-sila-difenidol hydrochloride $M_4$ Pirenzepine, Telenzepine.

Analogs of the foregoing compounds that function as muscarinic agonists are also specifically intended to be embraced by the present invention. The ability of such analogs to restore the resting position of the eye and allow normal positive and negative accommodation can be tested easily using no more than routine experimentation.

The method in accordance with the present invention is suited particularly for subjects who are otherwise free of indications for ophthalmic treatments utilizing a muscarinic agonist.

The muscarinic agonists in accordance with the present invention may be administered per se or in the form of a pharmaceutically acceptable salt. When used in a formulation, the salts of muscarinic agonists should be both pharmacologically and pharmaceutically acceptable, but non-pharmaceutically acceptable salts may be conveniently used to prepare the active free compound or pharmaceutically acceptable salts thereof.

Many of the compounds of the present invention are known in the art for their purposes, and are known to be safe under ordinary conditions of use. Thus, the treatment of this invention can be administered by substantially conventional means, consistent with known eye treatments, and while avoiding irritation, discomfort of the need for unusual application procedures.

Formulation of the present invention may include any formulation which the compounds of the invention may be delivered to the eye. Preferably, the muscarinic agonists of the present invention are applied to the eye in a topical preparation. By a topical preparation, it is meant a preparation which is adapted to be applied to the surface of the eye. In such a preparation, therapeutic compounds of the preparation contact the surface of the eye and penetrate into the deeper tissues of the eye. Such preparations usually have liquid carriers which can be aqueous solutions or suspensions.

Preferably, the muscarinic agents in accordance with the present invention may be provided in formulations which enhance the duration of activity of the muscarinic agent on neuro-effective junctions. Accordingly, such formulations may include any of the hereinabove identified muscarinic agonists and antagonists.

The compounds of the present invention may be applied in pharmaceutically acceptable ophthalmic preparation, meaning preparation which produces medically desirable therapeutic effects without concurrently causing clinically significant adverse effects. Clinically significant effects refer to unacceptable side effects of the preparation, including either medically or cosmetically acceptable effects. Examples of unacceptable side effects include reddening or irritated eyes, impaired long distance vision, elevated intraocular pressure, or browache.

With particular reference to pilocarpine, the doses utilized in the present invention fall below that which would cause such side effects.

The compounds of the present invention are administered in therapeutically effective amounts. A therapeutic effective amount is one which causes a restoration of the resting position of the eye and allows normal positive and negative accommodation. Compounds are typically added to the ophthalmic preparations of the invention in concentrations of between about 0.001% and about 4% by weight of the entire formulation.

The compounds of the present invention are preferably administered topically and delivered in a medically acceptable, substantially sterile, non-irritating ophthalmic preparation. The ophthalmic preparations may routinely contain pharmaceutically acceptable concentrations of salts, buffering agents, preservatives, viscosity, modifiers, osmotic agent and delivery enhancing agents.

Salts which can be used include but are not limited to sodium chloride, zinc sulfate, and potassium chloride. Buffers which can be used include but are not limited to boric acid and citric acid. Preservatives which can be used include but are not limited to benzalkonium chloride and edetate disodium. Viscosity modifiers which can be used include but are not limited to methyl cellulose, glycerol, and polyethylene glycol. Osmotic agents which can be used include but are not limited to mannitol and sorbitol. Delivery enhancing agents that facilitates the delivery of the therapeutic compound of the invention into the aqueous humor, include substances which increase corneal permeability, such as surfactants, wetting agents, liposomes, DMSO, and the like. A wetting agent is a substance which facilitates corneal penetration by mildly disrupting the outer corneal surface. A preferred wetting agent is benzalkonium chloride. Other examples of wetting agents include sorbitan esters, and polyoxyethylene ethers.

It should be understood that although specific formulations have been defined, many variations are possible. In all cases, the ophthalmic formulations useful in the eye are nonirritating and nondamaging to the eye in the preferred form, and are effective to provide the results desired. Normally, such formulations can be applied in a liquid carrier, with an aqueous carrier being preferred although in some instances, quick dissolving forms of the medicaments may be administered in powder form or rubbed into the eye from applicators of various types. Spraying of the eye, eye drops, and other methods of application can be used.

Dosage levels will vary greatly depending upon the individual to be treated and the specific medicament used. Proper dosing can be determined without undue experimentation and according to procedures well known to those of ordinary skill in the art.

Humans may be characterized as having a mean amplitude of accommodation (measured in diopters) that decreases steadily with age. The methods of this invention are useful with subjects having a maximal dioptric power of 10 or less, preferably with subjects having a maximal dioptric power of 6 or less, and most preferably with subjects having a maximal dioptric power of 4 or less.

The preparations are preferably to be packaged as sterile solutions in dropper bottles, as are well known in the trade. Other containers, including eye cups, can also be used. The preparation is preferably packaged with instructions for using the preparation in treating presbyopia, typically directing the use of the preparation to administer 1 to 2 drops of the solution to each eye.

In a specific example of this invention, a base solution can be formulated as follows: Sodium Chloride 0.3%; Edetate Disodium 0.1%; Boric Acid 1.0%; Benzaliconium Chloride 0.01% Sodium Hydroxide (adjust to pH 6.4) and Water. Pilocarpine, at a concentration of 0.1% weight/volume, is added to the base solution.

The above formulation is administered to the eye of a 50-year old human adult with presbyopia, shown by his discomfort when reading, or his inability to read fine print. Vision is improved after administration of the eye drops.

When other muscarinic agonists are substituted for pilocarpine, similar results are obtained.

Further studying has been conducted to evaluate the effect of low dose muscarinic agents on the refractive state of the eye in both myopic and hyperopic presbyopic subjects.

Study Purpose

This clinical study was designed to evaluate the effect of a low dose muscarinic agent such as Pilocarpine from 0.001% to less than 2% by weight values on the refractive status of the eye.

Study Design

One drop of Pilocarpine 0.3% was administered topically to the eye of a presbyopic myope and hyperope, before and after Hartinger Refractometry at distance and near was performed by the same observer.

Materials and Methods
A. Materials
1. Pilocarpine 0.3%
2. Hartinger Refractometer
B. Methods
Preoperative Evaluation Refraction at distance and near was performed with the Hartinger Refractomer by the same observer prior to installation of Pilcarpine 0.3%. Three measurements were taken at distance and at near for each eye tested at each timepoint.

In the myopic presbyope, both eyes received Piolcarpine 0.3%. In the hyperopic presbyope, only the right eye received Pilocarpine 0.3%.

At approximately 30–50 and 60–90 minutes post installation of Pilocarpine, refraction measurements were repeated. The results are shown in Tables 1 and 2 and summarized in tables 3 and 4.

Results
Myopic Presbyope

At baseline prior to installation of Pilocarppine, refraction measured −1.25±0.0 in the right eye and −1.53 D in the left dyd (range −1.25 to −1.75) at distance.

Refraction at near was −2.0 D in the right eye (range −1.5 to −2.5) with a +1.75 sphere in the left eye for near fixation. Refraction measured −1.5 to −2.5) with a +1.75 sphere in the left eye for near fixation. Refraction measured −1.4 D in the left eye (range −1.0 to −2.0) with a +a1.50 sphere in the right eye for near fixation.

At 30 minutes post installation Pilocarpine 0.3%, refraction measured −1.06D in the right eye (range −1.0 to −1.1) and −4.2D in the left eye (range −1.25 to −1.50) at distance. Refraction at near was −1.8D in the right eye (range −1.6 to −2.0) with a +1.75 sphere in the left eye for near fixation. Refraction measured −1.53D in the left eye (range −1.5 to −1.6) with a +1.50 sphere in the right eye for near fixation.

At 60 min post installation of Pilocarpine 0.3%, refraction measured −1.05D in the right eye (range −1.0 to −1.1) and −1.25D+0.0 in the left eye at distance.

TABLE 1

Myopic Presbyope
Refraction (diopters)

| Time | Distance OD | Distance OS | Near OD | Near OS |
|---|---|---|---|---|
| Baseline, 2:00 pm | −1.25 | −1.75 | −2.50 | −1.00 |
|  | −1.25 | −1.60 | −1.50 | −2.00 |
|  | −1.25 | −1.25 | −2.00 | −1.40 |
| Pilo.3%, 2:25 pm |  |  |  |  |
| 30 min, 2:55 pm | −1.10 | −1.25 | −1.8 | −1.6 |
|  | −1.00 | −1.50 | −2.0 | −1.5 |
|  | −1.10 | −1.50 | −1.6 | −1.5 |
| 30 min, 3:45 pm | −0.9 | −1.25 | −1.5 | −0.75 |
|  | −1.1 | −1.25 | −1.5 | −1.00 |
|  | −1.3 | −1.25 | −1.5 | −1.10 |
|  | −0.9 |  |  |  |

TABLE 2

Hyperopic Presbyope
Refraction (diopters)

| Time | Distance OD | Near OD |
|---|---|---|
| Baseline, 2:15 pm | +0.75 | +0.75 |
|  | +0.80 | +0.60 |
|  | +0.80 | +0.75 |
| Pilo.3%, 2:25 pm |  |  |
| 50 min, 3:15 pm | +1.20 | +0.25 |
|  | +1.00 | +0.00 |
|  | +1.25 | +0.25 |
| 90 min, 4:00 pm | +0.50 | +0.40 |
|  | +0.50 | +0.25 |
|  | +0.25 | +0.50 |

Refraction at near was −1.5D±0.0 in the right eye with a +1.75 sphere in the left eye for near fixation. Refraction measured −0.95D in the left eye (range −0.75 to −1.1) with a +1.50 sphere in the right eye for near fixation.

TABLE 3

Myopic Presbyope
Mean Refraction (diopters)

| Time | Distance OD | Distance OS | Near OD | Near OS |
|---|---|---|---|---|
| Baseline | −1.25 | −1.53 | −2.0 | −1.47 |
| 30 min | −1.06 | −1.42 | −1.8 | −1.53 |
| 60 min | −1.05 | −1.25 | −1.5 | −0.95 |

Hyperopic Presbyope

At baseline prior to installation of Pilocarpine, refraction measured +0.78D in the right eye (range +0.75 to +0.80) at distance.

Refraction at near was +0.7 D in the right eye (range +0.6 to +0.75) with a +2.50 sphere in the left eye for near fixation.

At 50 minutes post installation of Pilocarpine 0.3%, refraction measured +1.15 D in the right eye (range +1.0 to +1.25) at distance.

Refraction at near was +0.17 D in the right eyed (range 0.0 to +0.25) with a +2.5 sphere in the left eye for near fixation.

At 90 minutes post installation of Pilocarpine 0.3%, refraction measured +0.42 D in the right eye (range +0.25 to +0.5) in the right eye at distance.

Refraction at near was +0.38 D in the right eye (range +0.25 to +0.4) with a +2.50 sphere in the left eye for near fixation.

TABLE 4

Hyperopic Presbyope
Mean Refraction (diopters)

| Time | Distance OD | Near OD |
| --- | --- | --- |
| Baseline | +0.78 | +0.7 |
| 50 min | +1.15 | +0.17 |
| 90 min | +0.42 | +0.38 | no notable change in pupil size was observed.

DISCUSSION

In the present pilot study, a low dose muscarinic agent was administered before and after refraction at distance and near was objectively obtained by one observer using the Hartinger Refractomet. Pilocarpine 0.3% in known to act on both the circular and longitudinal cilaiary muscle and was administered at a dose that in not known to affect accommodation.

In the Myopic presbyope, a small but definite decrease in the distance and near myopic correction which was greater at 60 than 30 minutes post dosing was found. As both distance and near refraction changed to similar degrees and in the same direction, the data suggest a change in the neutral accommodative state (tonic accommodation). For example, the entire crystalline lens body may have moved more posterior, towards the retina.

In the Hyperopic presbyope, a small but definite decrease in the distance and near hyperopic correction was noted at 90 minutes post dosing. As both distance and near refraction changed to similar degrees and in the same direction, the date suggests a change in the neutral accommodative state (tonic accommodation), For example, the entire crystalline lens body may have moved more anterior, towards the cornea.

There was no observable effect on pupil size and Hartinger refractometry, which requires a pupil size of greater than 2 to 2.5 mm, was not affected.

CONCLUSION

As both distance and near refraction changed to similar degrees and in the same direction, the data suggest a change in the neutral accommodative state (tonic accommodation). In the myopic presbyope, the entire crystalline lens body may have moved more posterior, towards the retina, while in the hyperopic presbyope it may have moved more anterior, towards the cornea.

Although there has been hereinabove described a specific method in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for increasing or decreasing parasympathetic/cholinergic/ciliary tonic contraction in order to restore the resting position of the eye and allow normal positive and negative accommodation for both myopic presbyopes and hyperopic presbyopes, said method comprising administering to a presbyope an effective amount of from 0.001% to less than 2% by weight/volume of pilocarpine for effecting a net response in the parasympathetic system of ciliary muscle components.

2. The method according to claim 1 wherein the muscarinic agonist is administered topically to the eye in a pharmaceutically acceptable ophthalmic formulation.

3. The method according to claim 1 wherein the effective amount comprises about 0.3% by weight/volume of pilocarpine.

4. A method for increasing or decreasing parasymphathetic/cholingeric/ciliar tonic contraction in order to restore the resting position of the eye and allow normal positive and negative accommodation, said method comprising administering to myopic presbyope an effective amount of from 0.001% to less 2% by weight/volume of pilocarpine for effecting a net response in the parasympathetic system of ciliary muscle components.

5. The method according to claim 4 wherein the muscarinic agonist is administered topically to the eye in a pharmaceutically acceptable ophthalmic formulation.

6. The method according to claim 4 wherein the effective amount comprises about 0.3% by weight/volume of pilocarpine.

7. A method for increasing or decreasing parasympathetic/cholingeric/ciliary tonic concentration in order to restore the resting position of the eye and allow normal positive and negative accommodation, said method comprising administering to a hyperopic presobyope an effective amount of from 0.001% to less than 2% by weight/volume of pilocarpine for effecting a net response in the parasympathetic system of ciliary muscle components.

8. The method according to claim 7 wherein the muscarinic agonist is administered topically to the eye in a pharmaceutically acceptable ophthalmic formulation.

9. The method according to claim 7 wherein the effective amount comprise about 0.3% by weight/volume of pilocarpine.

10. A method for increasing or decreasing parasympathetic/cholingeric/ciliary tonic contraction in order to restore the resting position of the eye and allow normal positive and negative accommodation for both myopic presbyopes and hyperopic presbyopes, said method comprising administering to a presbyope an effective amount of pilocarpine for effecting a net response in the parasympathetic system of ciliary muscle components without effecting a change in pupil diameter.

11. The method according to claim 10 wherein the muscarinic agonist is administered topically to the eye in a pharmaceutically acceptable ophthalmic formulation.

12. The method according to claim 10 wherein the effective amount comprises between about 0.001% to at least about 2% by weight/volume of pilocarpine.

13. The method according to claim 1 wherein the effective amount comprises about 0.3% by weight/volume of pilocarpine.

* * * * *